United States Patent [19]

Andriacchi et al.

[11] 4,279,042

[45] Jul. 21, 1981

[54] HIP PROSTHESIS

[75] Inventors: Thomas P. Andriacchi, Chicago; Jorge O. Galante, Oak Brook; Steven J. Hampton, Villa Park, all of Ill.

[73] Assignee: Rush-Presbyterian-St. Luke's Medical Center, Chicago, Ill.

[21] Appl. No.: 97,410

[22] Filed: Nov. 26, 1979

[51] Int. Cl.³ .............................................. A61F 1/03
[52] U.S. Cl. ................................ 3/1.913; 128/92 CA
[58] Field of Search ........................... 3/1.913, 1.912; 128/92 C, 92 CA

[56] References Cited

U.S. PATENT DOCUMENTS

| | | | |
|---|---|---|---|
| 2,934,065 | 4/1960 | Townley | 128/92 CA |
| 4,004,300 | 1/1977 | English | 3/1.913 |
| 4,101,985 | 7/1978 | Baumann et al. | 3/1.912 |
| 4,141,088 | 2/1979 | Treace et al. | 3/1.912 |

FOREIGN PATENT DOCUMENTS 2705153  8/1978  Fed. Rep. of Germany ............ 3/1.913

Primary Examiner—Clifford D. Crowder
Attorney, Agent, or Firm—Fitch, Even, Tabin, Flannery & Welsh

[57] ABSTRACT

A femoral insert for a hip joint prosthesis wherein the proximal and distal portions are angularly joined to define a lateral apex, the apical height of which has a particular ratio to the medial length of the insert.

3 Claims, 7 Drawing Figures

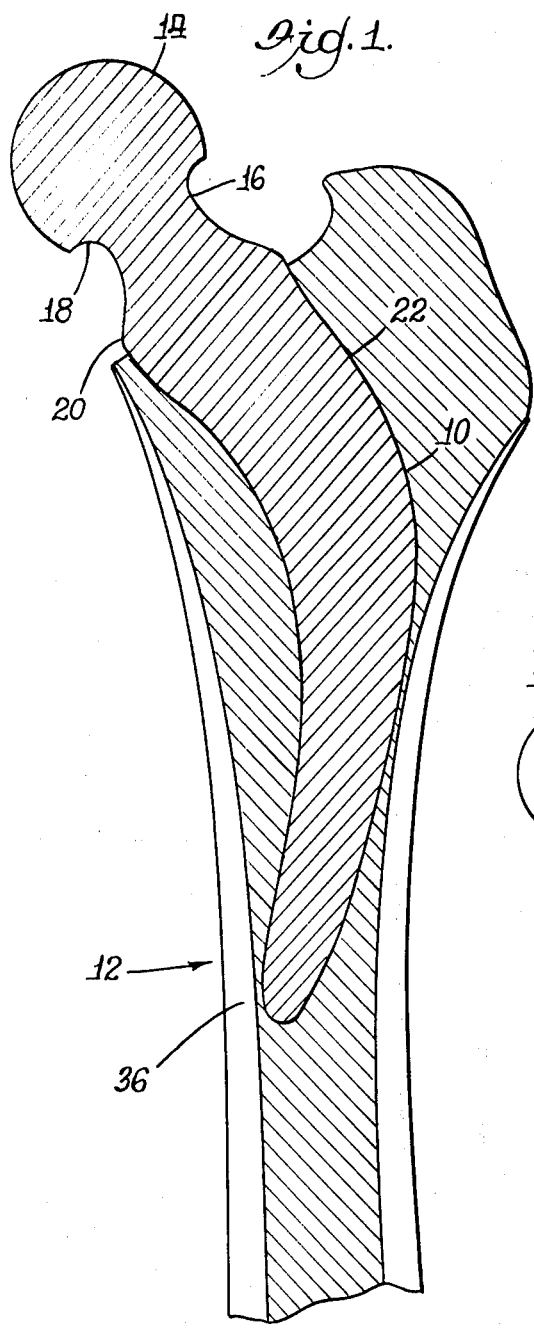
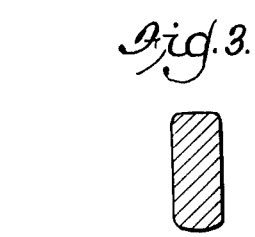
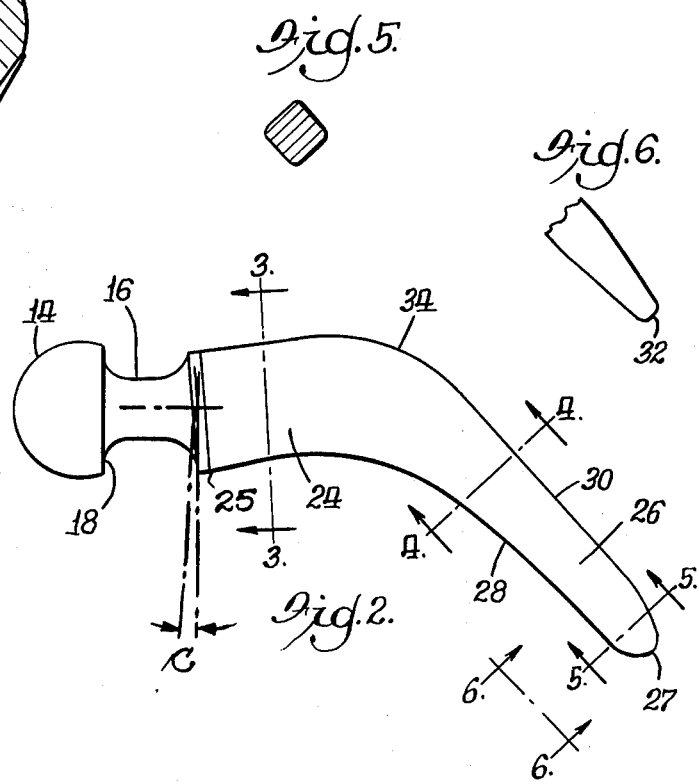
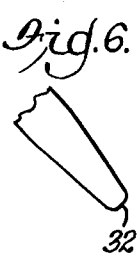
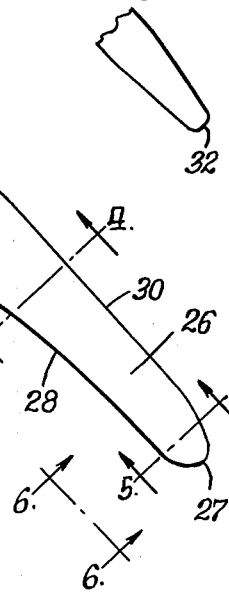
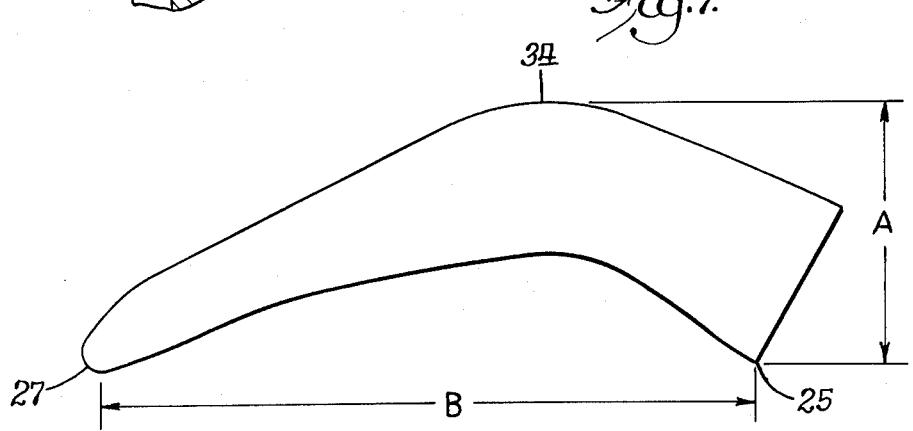

HIP PROSTHESIS

The invention described herein was made in the course of work under a grant or award from the Department of Health, Education and Welfare.

The present invention relates generally to the field of endoprosthetic devices and more particularly to improved femoral inserts for total hip replacement.

Successful clinical application of total hip replacement is one of the most important recent developments in orthopedic surgery. Indications for use, however, are still limited due to the many unknowns that influence the long term survival of these devices. At first glance, the potential for mechanical failure of these devices seems small. In its simplest form, the replacement comprises a cup member secured to the pelvis, by either a cement such as methyl methacrylate or by bone growth, a ball and a stem member secured within the intermedullary cavity of the femur, also either by a cement or bone growth. The ball is secured to the stem member and rotatably received by the cup member. Although the metal and plastic components have mechanical properties which appear to surpass those of the biological material being replaced, clinical experience has indicated that many of the failures of these devices, including component fractures, can be traced to mechanical causes, particularly in the stem.

Failure of these prosthetic devices requires surgical replacement. In addition to the normal concerns of any surgery, such replacement surgery is particularly undesirable because frequently portions of the biological material surrounding the failed device must be removed, thus, further weakening the overall structure. Therefore, there have been many efforts to reduce the frequency of failures requiring replacement.

Because very large stresses are developed in the stem, most efforts have been directed to development of improved materials and structural reinforcement of the stem. Unfortunately, however, there are certain parameters which strictly limit the choices of material and the structural reinforcement. In particular all materials used must be inert to biological fluids to prevent corrosion and rejection. In addition, the stem structure must be adapted for insertion within the femur, while preferably displacing only a minimal amount of biological material. Otherwise the femur is weakened to the point where fracture becomes a significant danger.

Although prior efforts in this field have been primarily directed to overcoming stresses by strengthening the stems in design and material, a different approach is instead to reduce the mechanical stresses applied to the femoral stem. In this manner, one may use previously used materials, known to be inert to body fluids and free of rejection problems.

It is therefore an object of the present invention to provide an improved femoral stem for a hip prosthesis which has improved resistance to failure while comprising presently used materials. It is also an object to provide a femoral stem which is subjected to reduced mechanical stresses. It is a further object to provide a femoral stem which requires a minimal removal of biological material for insertion.

Further objects and advantages will become apparent when the following detailed description is considered with reference to the accompanying drawings in which:

FIG. 1 is a lateral cross-sectional view of a femoral insert embodying various of the features of the present invention, secured in a femur.

FIG. 2 is an elevational view of a femoral insert embodying various of the features of the present invention.

FIG. 3 is a cross-sectional view of the femoral insert of FIG. 2, taken along line 3—3.

FIG. 4 is a cross-sectional view of the femoral insert of FIG. 2 taken along line 4—4.

FIG. 5 is a cross-sectional view of the femoral insert of FIG. 2, taken along line 5—5.

FIG. 6 is a partial elevational view of the femoral insert of FIG. 2, taken along line 6—6.

FIG. 7 is an elevational view of a femoral insert stem embodying various of the features of the present invention, resting medially upon a planar surface.

It has been found that the support of the stem by surrounding bone and cement is the most important factor in maintaining low stem stress. The stem derives support from all of the adjacent media, but most important is the stem support in the proximal medial region of the calcar and the support on the lateral surface of the stem. The stem must be supported by stiff media in the region of the calcar. Because the cements used, i.e. primarily methyl methacrylate, are generally less stiff than cortical bone, this means that the stem should rest directly upon cortical bone or on a thin layer of cement between the stem and cortex in this region.

It was also found that the location of the lateral cortical support of the stem is an important factor in reducing stem stresses. This support should be placed as proximal as possible based on anatomical restraints. A proximal lateral support of the stem moves the resultant constraint force more proximally, thus distributing bending stresses in the proximal portion of the stem, which has a larger cross-section than the distal stem.

Analysis has also shown that there is a tendency for the stem to rotate in the cement about an axis perpendicular to the plane of the stem. The stem rotates until the media supporting the lateral surface of the stem can resist the load. Since the cement is relatively soft, compared to the cortex and the stem material, the stem rotates to bring the distal portion of the stem closer to the cortex. To prevent this rotation from resulting in a dangerously distal result, the stem of the present invention is designed so that the lateral surface very nearly contacts the lateral cortex proximally and then curves away from this cortex, approaching the other side of the cortex distally. Thus, as a result, the most stiff media is laterally adjacent to the stem in the proximal region of the stem. Furthermore, the lateral contact of the distal stem portion with the cortex serves to prevent subsidence of the stem.

In sum, it has been found that an angular femoral prosthesis, having a three-point cortical contact, has improved support and reduced stresses applied thereto. Such femoral prosthesis may be constructed of known biologically inert materials and in sizes requiring minimal removal of biological material.

Referring more particularly to the drawings, in FIG. 1 there is shown a femoral insert 10 within a femur 12. The femoral insert 10 includes a convex spherical head 14 adapted for rotational reception by a cup-shaped acetabulum prosthesis (not shown). The head 14 is axially secured to an elongated neck 16 at one end 18. At the opposing end 20 of the neck 16, a stem 22 is secured. Preferably, the interface between the stem 22 and the axis of the neck 16, form an angle C of from 0° to about 5°.

Generally, the stem 22 comprises a proximal portion 24 having a proximal medial endpoint 25 and a distal portion 26 having a distal media endpoint 27, the proximal portion being secured to the neck 16. The distal portion 26 forms an angular continuation of the proximal portion 24.

The stem 22 is generally rectangular in cross-section, however, the medial side is rounded, as shown particularly in FIGS. 3 and 4.

Although stem sizes may be varied to adapt to variably sized femurs, in one embodiment, the proximal portion 24 is generally constant in cross-section, approximately 1.0 inch by 0.4 inch. There is no collar or overhang of the stem at the neck end 20. The distal portion 26 tapers gradually along the medial side 28 and remains generally linear along the lateral side 30. At the point defined by the line 4—4 in FIG. 2, the dimensions are about 0.75 inch to 0.4 inch. At the point defined by the line 5—5 in FIG. 2, the dimensions are about 0.4 inch by 0.3 inch. As shown in FIG. 6, the distal portion 26 tapers in both cross-sectional dimensions as it approaches the distal tip 32, which is generally rounded.

As noted above, the proximal portion 24 and the distal portion 26 are angularly joined to form a generally curved shape. At the junction of the portions 24 and 26 an apex 34 is formed.

Referring to FIG. 7, in a femoral stem in accordance with the present invention, the ratio between the apical height A and the medial length B is between about 0.35 and 0.42. The exact ratio depends primarily upon the stem size required for the particular femur involved. Stem sizes are selected so that the desired relationship of three point contact between the stem and femur can be achieved for the most anatomical configurations. The only significant change necessary for proper fit is the length of the proximal portion of the stem. The curved distal portion of the stem is oriented in the desired manner for any size medullary canal, leaving only the proximal portion to be varied for different proximal femur configurations.

During implantation of any femoral stem, an important concern for a surgeon is a proper cut of the neck of the femur. For stems having collars, the angle and level of cut is critical and the neck of the femur may be cut several times to achieve proper orientation. A collarless stem obviates this concern.

When an essentially linear stem is used, the surgeon must be concerned with the pivotal orientation of the stem in a horizontal plane. Even if the reaming is performed properly, a generally linear stem often will rotate when inserted into the cement-filled canal. The reaming procedure for implanting stems in accordance with the present invention is designed to ensure proper orientation. After removal of the femoral neck, a calibrated reamer with a curvature identical to the actual insert is introduced close to the calcar and directed toward the lateral cortex. As it reaches the lateral cortex, the curved shape forces the reamer to slide towards the medial cortex 36. As in all reaming of femur, the surgeon must ensure that the reamer tip does not penetrate the cortex either laterally or medially. Cement is then applied to the reamed canal. When the stem is inserted it is forced to follow the pre-reamed canal, no other position being possible. The stem slides on the calcar, towards the lateral cortex and then angles medially, ultimately contacting the medial cortex. Thus the desired three triangular contact points are formed: in the calcar region, the lateral cortex and the medial cortex. Moreover, the lateral cortical contact point is at a point in the proximal portion. Bending stresses are applied to the proximal portion which has a greater cross-section than the distal portion.

Although the invention has been illustrated and described with regard to certain preferred embodiments, it should be understood that changes and modifications as would be obvious to one having ordinary skill in the art may be made without departing from the scope of the invention which is defined solely by the appended claims. Various of the features of the invention are set forth in the claims which follow.

What is claimed is:

1. A femoral insert for a hip joint prosthesis, comprising a convex spherical head axially secured to a collarless elongated neck and a stem secured to said neck opposite from said head, said stem including a proximal portion having a proximal medial endpoint, and a distal portion having a distal medial endpoint, said proximal portion and said distal portion being angularly joined to define a lateral apex having an apical height, said proximal medial endpoint and said distal medial endpoint defining a medial length, the ratio of said apical height to said medial length being greater than about 0.35.

2. A femoral insert in accordance with claim 1 wherein said ratio between said apical height and said medial length is between about 0.35 and 0.42.

3. A femoral insert in accordance with claim 1 wherein said stem is generally rectangular in cross-section, and said proximal portion has a generally constant cross-section.

* * * * *